United States Patent [19]

Kast et al.

[11] Patent Number: 5,411,936
[45] Date of Patent: May 2, 1995

[54] CYCLOHEXENONE OXIME ETHERS, AND THEIR USE AS HERBICIDES

[75] Inventors: Juergen Kast, Boehl-Iggelheim; Dieter Kolassa, Ludwigshafen; Norbert Meyer, Ladenburg; Ulrich Schirmer, Heidelberg; Albrecht Harreus, Ludwigshafen; Jochen Wild, Deidesheim; Karl-Otto Westphalen, Speyer; Bruno Wuerzer, Otterstadt, all of Germany

[73] Assignee: BASF Aktiengesellschaft, Ludwigshafen, Germany

[21] Appl. No.: 5,428

[22] Filed: Jan. 19, 1993

Related U.S. Application Data

[60] Continuation of Ser. No. 640,220, Jan. 11, 1991, abandoned, which is a division of Ser. No. 429,451, Oct. 31, 1989, Pat. No. 5,022,914.

[30] Foreign Application Priority Data

Nov. 11, 1988 [DE] Germany ............ 38 38 309.8

[51] Int. Cl.$^6$ ............ C07C 255/34; C07C 251/38; C07D 213/84; A01N 43/40
[52] U.S. Cl. ............ 504/244; 504/310; 504/318; 504/344; 546/286; 546/287; 546/288; 546/300; 546/329; 546/330; 546/335; 546/342; 558/418; 558/419; 558/422; 564/256; 564/264; 560/21; 560/37
[58] Field of Search ............ 549/426, 417, 416, 356; 504/244, 310, 318, 344; 546/286, 287, 288, 300, 329, 330, 342; 558/418, 419, 422; 564/256, 264; 560/21, 37

[56] References Cited

U.S. PATENT DOCUMENTS 3,950,420  4/1976  Sawaki et al. ............ 546/301
4,602,935  7/1986  Becker et al. ............ 504/292

*Primary Examiner*—Alan L. Rotman
*Attorney, Agent, or Firm*—Keil & Weinkauf

[57] ABSTRACT

Cyclohexenone oxime ethers of the general formula I

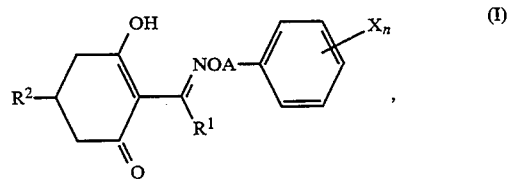

where $R^1$ is $C_1$–$C_6$-alkyl, A is substituted or unsubstituted $C_4$-alkylene or $C_4$-alkenylene, x is nitro, cyano, halogen, $C_1$–$C_4$-alkyl, $C_1$–$C_4$-alkoxy, $C_1$–$C_4$-alkylthio, $C_1$–$C_4$-haloalkyl, $C_1$–$C_4$-haloalkoxy, carboxyl, $C_1$–$C_4$-alkoxycarbonyl, substituted or unsubstituted benzyloxycarbonyl and/or phenyl, n is from 0 to 3 or from 1 to 5 when X is halogen, $R^2$ is $C_1$–$C_6$-alkoxy-$C_1$–$C_6$-alkyl or $C_1$–$C_4$-alkylthio-$C_1$–$C_6$-alkyl, substituted or unsubstituted $C_3$–$C_7$-cycloalkyl or $C_5$–$C_7$-cycloalkenyl, a substituted or unsubstituted 5-membered saturated heterocyclic radical which contains one or two oxygen and/or sulfur atoms as heteroatoms, a substituted or unsubstituted 6- or 7-membered heterocyclic radical which contains one or two oxygen and/or sulfur atoms and one or two double bonds, a substituted or unsubstituted 5-membered heteroaromatic radical containing one or two nitrogen atoms and an oxygen or a sulfur atom, substituted or unsubstituted phenyl or pyridyl, and their agriculturally useful salts and esters of $C_1$–$C_{10}$-carboxylic acids and inorganic acids, methods of manufacturing them, and their use as herbicides.

3 Claims, No Drawings

CYCLOHEXENONE OXIME ETHERS, AND THEIR USE AS HERBICIDES

This application is a continuation of application Ser. No. 07/640,220, filed on Jan. 11, 1991, abandoned which is a division application of Ser. No. 07/429,451, filed on Oct. 31, 1989, now U.S. Pat. No. 5,022,914.

The present invention relates to novel herbicidal cyclohexenone oxime ethers of the formula I

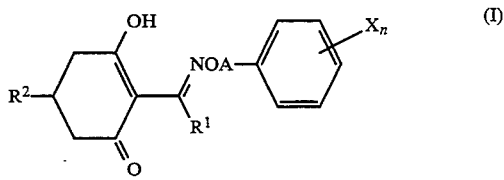

where $R^1$ is $C_1$-$C_6$-akyl, A is $C_4$-alkyl or $C_4$-alkenyl chain and these chains may carry from one to three $C_1$-$C_3$-alkyl groups and/or halogen atoms, X is nitro, cyano, halogen, $C_1$-$C_4$-alkyl, $C_1$-$C_4$-alkoxy, $C_1$-$C_4$-alkylthio, $C_1$-$C_4$-haloalkyl, $C_1$-$C_4$-haloalkoxy, carboxyl, $C_1$-$C_4$-alkoxycarbonyl, benzylocarbonyl and/or phenyl, and the aromatic radicals may carry from one to three of the following substituents: nitro, cyano, halogen, $C_1$-$C_4$-alkyl, $C_1$-$C_4$-alkoxy, $C_1$-$C_4$-alkylthio, $C_1$-$C_4$-haloalkyl, $C_1$-$C_4$-haloalkoxy, carboxyl, $C_1$-$C_4$-alkoxycarbonyl and/or benzyloxycarbonyl, n is from 0 to 3 or from 1 to 5 if X is halogen, $R^2$ is $C_1$-$C_4$-alkoxy-$C_1$-$C_4$-alkyl or $C_3$-$C_7$-cycloalkenyl, and these groups, may carry from one to three of the following substituents $C_1$-$C_4$-alkyl, $C_1$-$C_4$-alkoxy, $C_1$-$C_4$-alkylthio, $C_1$-$C_4$-haloalkyl, hydroxyl and/or halogen, a 5-membered saturated heterocyclic radical which contains one or two oxygen and/or sulfur atoms as heretoatoms and may carry from one to three of the following groups: $C_1$-$C_4$-alkyl, $C_1$-$C_4$-alkoxy, $C_1$-$C_4$-alkylthio and/or $C_1$-$C_4$-haloalkyl, a 6-membered or a 7-membered heterocyclic radical containing one or two oxygen and/or sulfur atoms and one or two double bonds, and this ring may carry from one to three of the following subsituents: hydroxyl, halogen, $C_1$-$C_4$-alkyl, $C_1$-$C_4$-alkoxy, $C_1$-$C_4$-alkylthio and/or $C_1$-$C_4$-haloalkyl, a 5-membered heteroaromatic radical containing one or two nitrogen atoms and an oxygen atom or a sulfur atom, and this ring may carry from one to three of the following substituents: halogen, cyano, $C_1$-$C_4$-alkyl, $C_1$-$C_4$-alkoxy, $C_1$-$C_4$-alkylthio, $C_1$-$C_4$-haloalkyl, $C_2$-$C_6$-alkenyl, $C_2$-$C_6$-alkenyloxy, $C_2$-$C_6$-haloalkenyl and/or $C_1$-$C_4$-alkoxy-$C_1$-$C_4$-alkyl, phenyl or pyridyl and these groups may carry from one to three of the following substituents: halogen, nitro, cyano, $C_1$-$C_4$-alkyl, $C_1$-$C_4$-alkoxy, $C_1$-$C_4$-alkylthio, $C_1$-$C_4$-haloalkyl, $C_3$-$C_6$-alkenyloxy, $C_3$-$C_6$-alkynyloxy and/or —$NR^3R^4$, where $R^3$ is hydrogen, $C_1$-$C_4$-alkyl, $C_3$-$C_6$-alkenyl or $C_3$-$C_6$-alkynyl and $R^4$ is hydrogen, $C_1$-$C_4$-alkyl, $C_3$-$C_6$-alkenyl, $C_3$-$C_6$-alkynyl, $C_1$-$C_6$-acyl or benzoyl, and the aromatic ring may carry from one to three of the following substituents: nitro, cyano, halogen, $C_1$-$C_4$-alkyl, $C_1$-$C_4$-alkoxy, $C_1$-$C_4$-alkylthio and/or $C_1$-$C_4$-haloalkyl, and their agriculturally useful salts and esters of $C_1$-$C_{10}$-carboxylic acids and inorganic acids.

The present invention furthermore relates to a process for their preparation and their use as crop protection agents.

The novel cyclohexenones I are evidently acidic, ie. they can form simple reaction products such as salts of alkali metal or alkaline earth metal compounds or enol esters.

The compounds of the formula I may occur in a plurality of tautomeric forms, all of which are claimed.

In the literature, cyclohexenones of the general formula I'

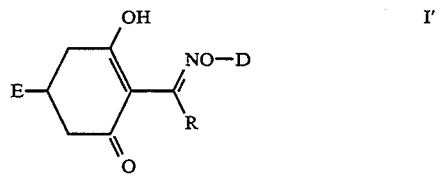

where, inter alia, D is benzyl and E is 2-ethylthiopropyl (U.S. Pat. No. 4,440,566), D is benzyl or but-2-enyl and E is a substituted 5-membered hetaryl radical (EP-A 238 021 and EP-A 125 094), D is benzyl or but-2-enyl and E is a substituted phenyl (EP-A 80 301) and D is but-2-enyl and E is a 5-membered to 7-membered heterocyclic ring having up to two O or S atoms and up to two double bonds (EP-A 218 233), are described as herbicides.

It is an object of the present invention to provide compounds which have high selectivity at a low application rate, ie. control undesirable plants without damaging the crops.

We have found that this object is achieved by the novel cyclohexenone oxime ethers of the formula I, which have a good herbicidal action against undesirable grasses. The compounds are tolerated by broad-leaved crops and some of them by gramineous crops such as rice.

The cyclohexenones of the formula I can be prepared in a known manner from known derivatives of the formula II (EP-A 80 301, EP-A 125 094, EP-A 142 741, U.S. Pat. No. 4,249,937, EP-A 137 174 and EP-A 177 913) and the corresponding hydroxylamines of the formula III (Houben-Weyl, 10/1, page 1181 et seq.) (EP-A 169 521).

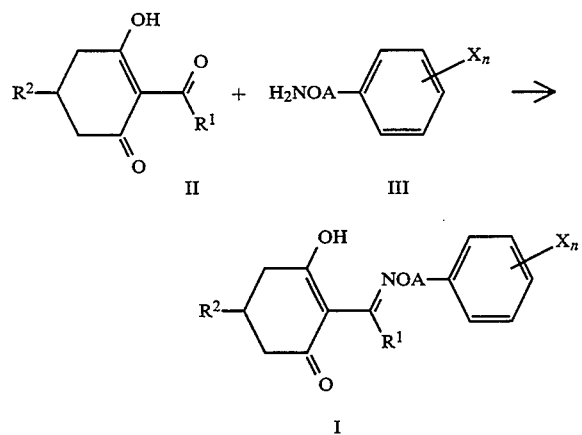

The reaction is advantageously carried out in the heterogeneous phase in a solvent at an adequate temperature below about 80° C., in the presence of a base, and the hydroxylamine III is used in the form of its ammonium salt.

Examples of suitable bases are carbonates, bicarbonates, acetates, alcoholares or oxides of alkali or alkaline earth metals, in particular sodiumhydroxide, potassium hydroxide, magnesium oxide and calcium oxide. It is also possible to use organic bases, such as pyridine or tertiary a mines. The base is added, for example, in an amount of from 0.5 to 2 mol equivalent, based on the ammonium compound.

Examples of suitable solvents are dimethyl sulfoxide, alcohols, such as methanol, ethanol and isopropanol, aromatic hydrocarbons, such as such as benzene and toluene, chlorohydrocarbons, such as chloroform and dichloroethane, aliphatic hydrocarbons, such as hexane and cyclohexane, esters, such as ethyl acetate, and ethers, such as diethyl ether, dioxane and tetrahydrofuran. The reaction is preferably carried out in methanol with sodium bicarbonate as the base.

The reaction is complete after a few hours. The target compound can be isolated, for example, by evaporating down the mixture, partitioning the residue in methylene chloride/water and distilling off the solvent under reduced pressure.

However, the free hydroxylamine base, for example in the form of an aqueous solution, can also be used directly for this reaction; a single-phase or two-phase reaction mixture is obtained, depending on the solvent used for the compound II.

Suitable solvents for this variant are, for example, alcohols, such as methanol, ethanol, isopropanol and cyclohexanol, aliphatic and aromatic hydrocarbons and chlorohydrocarbons, such as hexane, cyclohexane, methylene chloride, toluene and dichloroethane, esters, such as ethyl acetate, nitriles, such as acetonitrile, and cyclic ethers, such as dioxane and tetrahydrofuran.

Alkali metal salts of compounds I can be obtained by treating the 3-hydroxycompound with sodium hydroxide, potassium hydroxide, sodium alcoholate or potassium alcoholate in aqueous solution or in an organic solvent, such as methanol, ethanol, acetone or toluene.

Other metal salts, such as manganese, copper, zinc, iron, calcium, magnesium and barium salts, can be prepared from the sodium salts in a conventional manner, as can ammonium and phosphonium salts, using ammonia, phosphonium, sulfonium or sulfoxonium hydroxides.

The compounds of type II can be prepared, for example, from the corresponding cyclohexane-1,3-diones of the formula IV

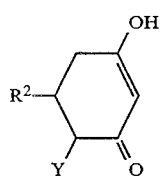

IV where Y is hydrogen or methoxycarbonyl, by a known method (Tetrahedron Lett., 2491 (1975)).

It is also possible to prepare the compounds of the formula II via the enol ester intermediate V, which is obtained in the reaction of a compound of the formula IV with an acyl chloride VI in the presence of a base and subsequently undergo a rearrangement reaction with certain imidazole or pyridine derivatives (Japanese Preliminary Published Application 79/063 052).

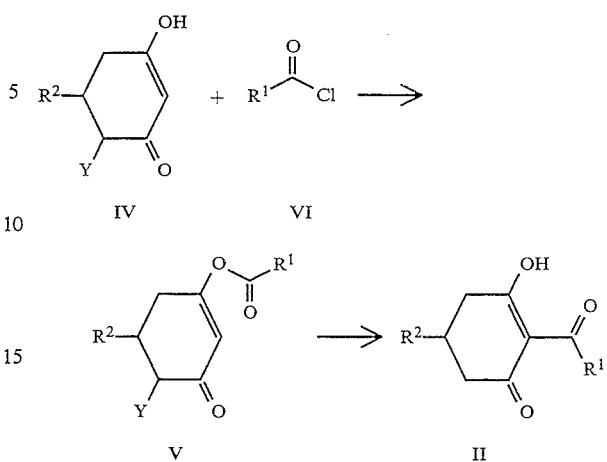

The compounds of the formula IV are obtained via a number of known process steps, starting from known intermediates.

The synthesis of the hydroxylamines III in which A is a substituted or unsubstituted but-2-enylene bridge is carried out according to the reaction scheme below, starting from aniline derivatives IV, by diazotization followed..by coupling of the diazonium salt to an appropriately substituted butadiene V. The resulting mixture of VIa and VIb is coupled to a cyclic hydroxyimide VII, and the resulting protected hydroxylamine derivative VIII is cleaved with 2-aminoethanol to give the free hydroxylamine III.

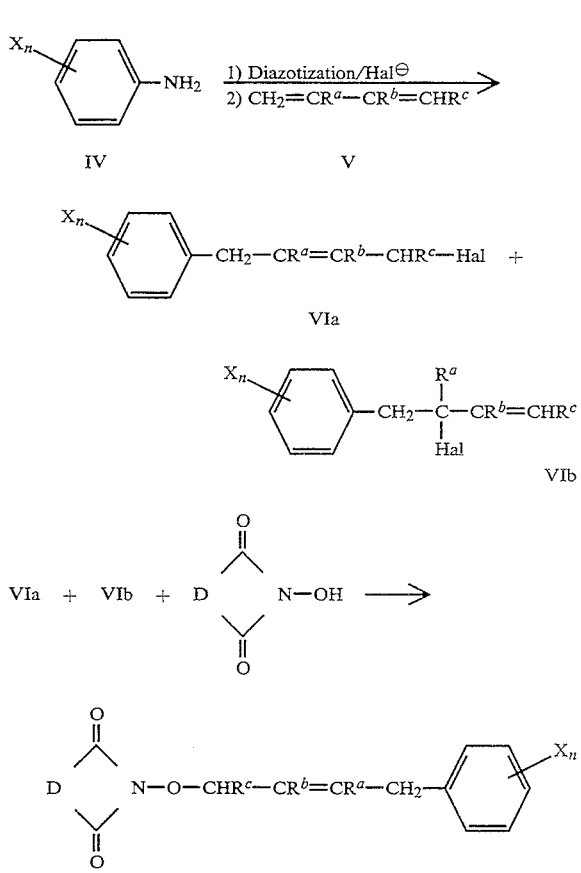

-continued

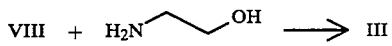

$R^a$, $R^b$ and $R^c$ independently of one another are each hydrogen, $C_1$–$C_3$-alkyl and/or halogen. Hal is halogen, preferably chlorine.

Examples of suitable cyclic hydroxyimides are the following substances t

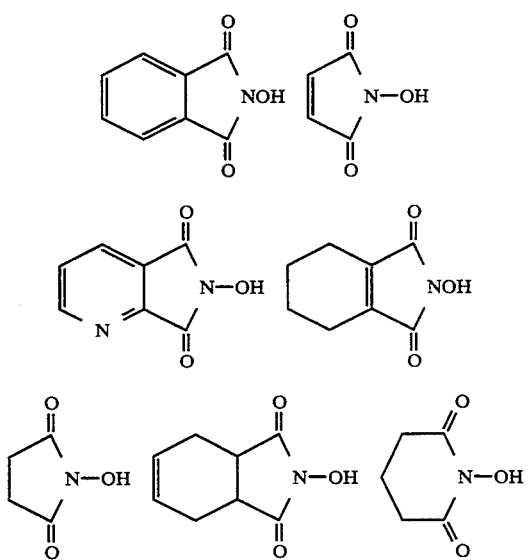

The halides VIa required for the synthesis of the novel hydroxylamines of the formula III can be prepared, as a mixture with VIb, by processes known from the literature, for example by reacting diazonium salts of aromatic and heteroaromatic anilines with dienes. The range of applications of the reaction is discussed in Organic Reactions 11 (1960), 189 and 24 (1976), 225.

Coupling of the isomeric halides VIa and VIb to a cyclic hydroxyimide of the formula VII gives exclusively the cyclic imide ethers of the formula VIII, which give the hydroxylamines III after the protective group at the nitrogen has been eliminated.

The reaction of the mixture of VIa and VIb with a hydroxyimide VIII is carried out in the presence of an acid acceptor and of a solvent. For reasons of cost, hydroxyphthalimide is preferably used as the hydroxyimide VIII.

Suitable acid acceptors are alkali metal carbonates, such as potassium carbonate and sodium carbonate, alkali metal bicarbonates, such as potassium bicarbonate and sodium bicarbonate, tertiary amines, such as trimethylamine and triethylamine, and basic heterocycles, such as pyridine. For cost reasons, potassium carbonate and sodium carbonate are preferred.

Suitable solvents are aprotic dipolar organic solvents, such as dimethylformamide, dimethyl sulfoxide and/or sulfolane.

Alkylation under phase-transfer conditions is also possible. The organic solvents used here are water-immiscible compounds, such as hydrocarbons or chlorohydrocarbons. Suitable phase-transfer catalysts are quaternary ammonium and phosphonium salts.

The cyclic imide ether VIII is cleaved with an alkanolamine by a process similar to that described in EP-A 244 786. The hydroxylamines III can be isolated by this process as free bases or, after precipitation with acids, as salts. Readily crystallizing salts are obtained by reacting the bases with oxalic acid.

With regard to the biological activity, preferred cyclohexenones of the formula I are those in which the substituents have the following meanings: $R^1$ is alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl, in particular ethyl and propyl, A is alkylene or alkenylene, such as butylene, but-2-enylene and but-3-enylene, which may be monosubstituted to trisubstituted, in particular, by methyl or ethyl and/or fluorine or chlorine, in the case of the unsaturated chains, both the cis and the trans form may occur. But-2-enylene is particularly preferred.

X is halogen, such as fluorine, chlorine, bromine or iodine, in particular fluorine or chlorine; alkyl, such as methyl, ethyl, propyl, 1-methylethyl, butyl, 1-methylpropyl, 2-methylpropyl or 1,1-dimethylethyl, in particular methyl or 1,1-dimethylethyl, alkoxy, such as methoxy, ethoxy, propoxy, 1-methylethoxy, butoxy, 1-methylpropoxy, 2-methylpropoxy and 1,1-dimethylethoxy, in particular methoxy, ethoxy, 1-methylethoxy or 1,1-dimethylethoxy, alkylthio, such as methylthio, ethylthio, propylthio, 1-methylethylthio, butylthio, 1-methylpropylthio, 2-methylpropylthio or 1,1-dimethylethylthio, in particular methylthio or ethylthio, haloalkyl, such as fluoromethyl, difluoromethyl, trifluoromethyl, chlorodifluoromethyl, dichlorofluoromethyl, trichloromethyl, 1-fluoroethyl, 2-fluoroethyl, 2,2-difluoroethyl, 2,2,2-trifluoroethyl, 2-chloro-2,2-difluoroethyl, 2,2-dichloro-2-fluoroethyl, 2,2,2-trichloroethyl and pentafluoroethyl, in particular difluoromethyl, trifluoromethyl, 2,2,2-trifluoroethyl or pentafluoroethyl, haloalkoxy, such as difluoromethoxy, trifluoromethoxy, chlorodifluoromethoxy, dichlorofluoromethoxy, 1-fluoroethoxy, 2-fluoroethoxy, 2,2-difluoroethoxy, 1,1,2,2-tetrafluoroethoxy, 2,2,2-trifluoroethoxy, 2-chloro-1,1,2-trifluoroethoxy or pentafluoroethoxy, in particular trifluoromethoxy, alkoxycarbonyl, such as methoxycarbonyl, ethoxycarbonyl, propoxycarbonyl, 1-methylethoxycarbonyl, butoxycarbonyl or 1,1-dimethylethoxycarbonyl, in particular methoxycarbonyl, ethoxycarbonyl or 1,1-dimethylethoxycarbonyl, specially methoxycarbonyl, and nitro, cyano, benzyloxycarbonyl or phenyl, where the aromatic radicals may in turn carry from one to three of the following radicalst nitro, cyano, carboxyl, benzyloxycarbonyl, halogen as stated in general and in particular for X, alkyl as stated for $R^1$, in particular methyl, ethyl or 1-methylethyl, alkoxy as stated above, in particular methoxy or ethoxy, alkylthio as stated above, in particular methylthio, haloalkyl as stated above, in particular trifluoromethyl, haloalkoxy as stated above, in particular difluoromethoxyor trifluoromethoxy, and/or alkoxycarbonyl as stated above, in particular methoxycarbonyl or ethoxycarbonyl.

Among these aromatic radicals, unsubstituted or monosubstituted ones are particularly preferred.

n is 0, 1, 2 or 3, in particular 0, 1 or 2. In the case of a plurality of radicals X, the substituents may be identical or different.

$R^2$ is alkyl as stated under $R^1$ and which may carry one of the alkoxy or alkylthio groups stated under X, preferably in the 1-, 2- or 3-position, in particular 2-ethylthiopropyl, 5-membered heterocycloalkyl, such as tetrahydrofuranyl, tetrahydrothiophenyl, dioxolanyl, dithiolanyl or oxathiolanyl, in particular tetrahydrofuranyl, tetrahydrothiophenyl or dioxolanyl, where these rings may carry from one to three of the $C_1$-$C_4$-alkyl, $C_1$-$C_4$-alkoxy, $C_1$-$C_4$-alkylthio and/or $C_1$-$C_4$-haloalkyl groups stated above under X, 5-membered hetaryl, such as pyrrolyl, pyrazolyl, imidazolyl, isoxazolyl, oxazolyl, isothiazolyl, thiazolyl, furanyl or thienyl, in particular isoxazolyl or furanyl, a 6-membered or 7-membered heterocyclic radical, such as tetrahydropyran- 3-yl, dihydropyran- 3-yl, tetrahydropyran-4-yl, dihydropyran-4-yl, tetrahydrothiopyran-3-yl, dihydrothiopyran-3-yl, tetrahydropyran-4-yl, dihydrothiopyran-4-yl and dioxepan-5-yl, in particular tetrahydropyran-3-yl, tetrahydropyran-4-yl or tetrahydrothiopyran-3-yl, phenyl or pyrridyl, and the cyclic radicals may carry from one to three of the alkyl, alkoxy, alkylthio and/or haloalkyl groups stated under X.

The 5-membered heteroaromatic radicals $R^2$ may carry the following substituents: halogen as stated under X, in particular fluorine or chlorine, alkoxyalkyl, such as methoxymethyl, 2-methoxyethyl, 2-methoxypropyl, 3-methoxypropyl, 2-methoxy-1-methylethyl, ethoxymethyl, 2-ethoxyethyl, 2-ethoxypropyl, 3-ethoxypropyl, 2-ethoxy- 1-methylethyl or 1-ethoxy- 1-methylethyl, in particular methoxyethyl or ethoxyethyl, alkenyl, such as ethenyl, 1-propenyl, 2-propenyl, 1-methylethenyl, 1-butenyl, 2-butenyl, 3-butenyl, 1-methyl-1-propenyl, 1-methyl-2-propenyl, 2-methyl-2-propenyl, 2-methyl-2-propenyl, 1-pentenyl, 2-pentenyl, 3-pentenyl, 4pentenyl, 1-methyl-1-butenyl, 2-methyl- 1-butenyl, 3-methyl-1-butenyl, 1-methyl-2-butenyl, 2-methyl-2-butenyl, 3-methyl-2-butenyl, 1-methyl-3-butynyl, 2-methyl-3-butenyl, 3-methyl-3-butenyl, 1,1-dimethyl-2-propenyl, 1-dimethyl-1-propenyl, 1,2-dimethyl-2-propenyl, 1-ethyl-1propenyl, 1-ethyl-2-propenyl, 1-hexenyl, 2-hexenyl, 3-hexenyl, 4-hexenyl, 5-hexenyl, 1-methyl- 1-pentenyl, 2-methyl-1-pentenyl, 3-methyl-1-pentenyl, 4-methyl- 1-pentenyl, 1-methyl-2-pentenyl, 2-methyl-2-pentenyl, 3-methyl-2-pentenyl, 4-methyl-2-pentenyl, 1-methyl-3pentenyl, 2-methyl-3-pentenyl, 3-methyl- 3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl- 1-butenyl, 1-ethyl- 1-butenyl, 1-ethyl-2-butenyl, 1-ethyl-3-butenyl, 2-ethyl-l-butenyl, 2ethyl-2-butenyl, 2-ethyl-3-butenyl, 1,1,2-trimethyl-2propenyl, 1-ethyl-l-methyl-2-propenyl, 1-ethyl-2-methyl-1-propenyl and 1-ethyl-2-methyl-2-propenyl, in particular 1-methylethenyl, or corresponding alkenyloxy and/or haloalkenyl.

The 6-membered and 7-membered heterocyclic radicals may also carry hydroxyl groups in addition to the abovementioned substituents.

In the phenyl and pyridyl radicals, the following radicals are also suitable substituents in addition to the abovementioned groups: alkenyloxy, such as 2-propenyloxy, 2-butenyloxy, 3-butenyloxy, 1-methyl-2-propenyloxy, 2-methyl-2-propenyloxy, 2-pentenyloxy, 3-pentenyloxy, 4-pentenyloxy, 1-methyl-2-butenyloxy, 2-methyl- 2-butenyloxy, 3-methyl - 2 -butenyloxy, 1-methyl- 3-butenyloxy, 2-methyl - 3-butenyloxy, 3-methyl-3-butenyloxy, 1,1-dimethyl-2-propenyloxy, 1,2-dimethyl-2-propenyloxy, 1-ethyl-2-propenyloxy, 2-hexenyloxy, 3-hexenyloxy, 4-hexenyloxy, 5-hexenyloxy, 1-methyl2-pentenyloxy, 2-methyl-2-pentenyloxy, 3-methyl-2-pentenyloxy, 4-methyl - 2-pentenyloxy, 1-methyl - 3-pentenyloxy, 2-methyl- 3-pentenyloxy, 3-methyl- 3-pentenyloxy, 4-methyl-3-pentenyloxy, 1-methyl-4-pentenyloxy, 2-methyl-4-pentenyloxy, 3-methyl-4-pentenyloxy, 4-methyl-4-pentenyloxy, 1,1-dimethyl-2-butenyloxy, 1,1-dimethyl - 3-butenyloxy, 1,2-dimethyl-2-butenyloxY, 1,2-dimethyl-3-butenyloxy, 1,3-dimethyi-2-butenyloxy, 1,3-dimethyl - 3-butenyloxy, 2,2 ,dimethyl - 3-butenyloxy, 2,3-dimethyl-2-butenyloxy, 2,3-dimethyl-3-butenyloxy, 1-ethyl-2-butenyloxy, 1ethyl-3-butenyloxy, 2-ethyl-2-butenyloxy, 2-ethyl-3-butenyloxy, 1,1,2-trimethyl-2-propenyloxy, 1-ethyl-1-methyl-2-propenyloxy and 1-ethyl-2-methyl-2-propenyloxy, in particular 2-propenyloxy and 2-butenyloxy, alkynyloxy, such 2-propynyloxy, 2-butynyloxy, 3-butynyloxy, 1-methyl-2-propynyloxy, 2-pentynyloxy, 3-pentynyloxy, 4-pentynyloxy, 1-methyl-3-butynyloxy, 2-methyl-3-butynyloxy, 1-methyl-2-butynyloxy, 1,1-dimethyl-2-propynyloxy, 1-ethyl-2-propynyloxy, 2-hexynyloxy, 3-hexynyloxy, 4-hexynyloxy, 5-hexynyloxy, 1-methyl-2-pentynyloxy, 1-methyl-3-pentynyloxy, 1-methyl-4-pentynyloxy, 2-methyl-3-pentynyloxy, 2-methyl-4-pentynyloxy, 3-methyl-4-pentynyloxy, 4-methyl-2-pentynyloxy, 1,1-dimethyl-2-butynyloxy, 1,1-dimethyl-3-butynyloxy, 1,2-dimethyl-3-butynyloxy, 2,2-dimethyl-3-butynyloxy, 1-ethyl-2-butynyloxy, 1-ethyl-3-butynyloxy, 2-ethyl-3-butynyloxy and 1-ethyl-1-methyl-2-propynyloxy, in particular 2-propynyloxy and 2-butynyloxy; amino, which may carry one or two of the following radicals: alkyl as stated for X, in particular methyl or ethyl, alkenyl as stated above, in particular 2-propenyl or 2-butenyl; alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-3-butynyl, 2-methyl-3-butynyl, 1-methyl-2-butynyl, 3-methyl- 1-butynyl, 1,1-dimethyl-2-propynyl, 1-ethyl-2-propynyl, 1-hexynyl, 2-hexynyl, 3-hexynyl, 4-alkynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl- 1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl, in particular 2-propynyl and 2-butynyl and/or acyl, such as acetyl, propionyl, isopropionyl, butyryl, 2-methylpropionyl, pentanoyl, 2-methylbutyryl, 3-methylbutyryl, 2,2-dimethylpropionyl, hexanoyl, 2-methylpentanoyl, 3-methylpentanoyl, 4-methylpentanoyl, 2,2-dimethylbutyryl, 2,3-dimethylbutyryl, 3,3-dimethylbutyryl or 2-ethylbutyryl, in particular acetyl or propionyl, or benzoyl.

Particularly preferred cyclohexenone oxime ethers of the formula I are summarized in the Tables below.

TABLE A

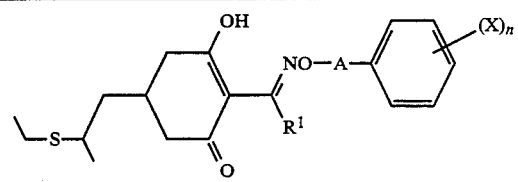

| R¹ | A | X |
|---|---|---|
| CH₂CH₃ | (CH₂)₄ | H |
| (CH₂)₂CH₃ | (CH₂)₄ | H |
| CH₂CH₃ | (CH₂)₂CH=CH | H |
| (CH₂)₂CH₃ | (CH₂)₂CH=CH | H |
| CH₂CH₃ | (CH₂)₄ | 4-CF₃ |
| (CH₂)₂CH₃ | (CH₂)₄ | 4-CF₃ |
| CH₂CH₃ | (CH₂)₄ | 3-F |
| (CH₂)₂CH₃ | (CH₂)₄ | 3-F |
| CH₂CH₃ | (CH₂)₄ | 4-F |
| (CH₂)₂CH₃ | (CH₂)₄ | 4-F |
| CH₂CH₃ | (CH₂)₄ | 3-CH₃ |
| (CH₂)₂CH₃ | (CH₂)₄ | 3-CH₃ |
| CH₂CH₃ | (CH₂)₄ | 4-OCH₃ |
| (CH₂)₂CH₃ | (CH₂)₄ | 4-OCH₃ |
| CH₂CH₃ | (CH₂)₄ | 3-NO₂ |
| (CH₂)₂CH₃ | (CH₂)₄ | 3-NO₂ |
| CH₂CH₃ | (CH₂)₄ | 3-CN |
| (CH₂)₂CH₃ | (CH₂)₄ | 3-CN |
| CH₂CH₃ | (CH₂)₄ | 3-CO₂CH₃ |
| (CH₂)₂CH₃ | (CH₂)₄ | 3-CO₂CH₃ |
| CH₂CH₃ | (CH₂)₄ | 3-CO₂Ph |
| (CH₂)₂CH₃ | (CH₂)₄ | 3-CO₂Ph |
| CH₂CH₃ | (CH₂)₄ | 4-OCHF₂ |
| (CH₂)₂CH₃ | (CH₂)₄ | 4-OCHF₂ |
| CH₂CH₃ | (CH₂)₄ | 3-CH₃,4-Cl |
| (CH₂)₂CH₃ | (CH₂)₄ | 3-CH₃,4-Cl |

TABLE B

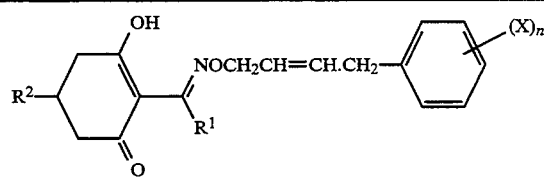

| R¹ | R² | X |
|---|---|---|
| CH₂CH₃ | tetrahydrofuran-3-yl (O) | H |
| (CH₂)₂CH₃ | tetrahydrofuran-3-yl (O) | H |
| CH₂CH₃ | tetrahydrofuran-3-yl (O) | 4-F |
| (CH₂)₂CH₃ | tetrahydrofuran-3-yl (O) | 4-F |
| CH₂CH₃ | tetrahydrofuran-3-yl (O) | 3-CH₃ |
| (CH₂)₂CH₃ | tetrahydrofuran-3-yl (O) | 3-CH₃ |

TABLE B-continued

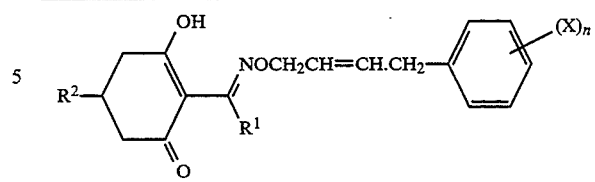

| R¹ | R² | X |
|---|---|---|
| CH₂CH₃ | tetrahydrofuran-3-yl (O) | 3-CF₃ |
| (CH₂)₂CH₃ | tetrahydrofuran-3-yl (O) | 3-CF₃ |
| CH₂CH₃ | tetrahydrofuran-3-yl (O) | 4-C(CH₃)₃ |
| (CH₂)₂CH₃ | tetrahydrofuran-3-yl (O) | 4-C(CH₃)₃ |
| CH₂CH₃ | tetrahydrofuran-3-yl (O) | 3-Cl |
| (CH₂)₂CH₃ | tetrahydrofuran-3-yl (O) | 3-Cl |
| CH₂CH₃ | tetrahydrothiophen-3-yl (S) | H |
| (CH₂)₂CH₃ | tetrahydrothiophen-3-yl (S) | H |
| CH₂CH₃ | tetrahydrothiophen-3-yl (S) | 4-F |
| (CH₂)₂CH₃ | tetrahydrothiophen-3-yl (S) | 4-F |
| CH₂CH₃ | tetrahydrothiophen-3-yl (S) | 3-CH₃ |
| (CH₂)₂CH₃ | tetrahydrothiophen-3-yl (S) | 3-CH₃ |
| CH₂CH₃ | tetrahydrothiophen-3-yl (S) | 3-CF₃ |
| (CH₂)₂CH₃ | tetrahydrothiophen-3-yl (S) | 3-CF₃ |

TABLE B-continued structure: cyclohexanone with OH, R², and C(R¹)=NOCH₂CH=CH.CH₂-phenyl-(X)ₙ substituent

| R¹ | R² | X |
|---|---|---|
| CH₂CH₃ | 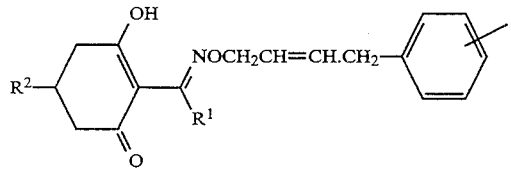 | 4-C(CH₃)₃ |
| (CH₂)₂CH₃ |  | 4-C(CH₃)₃ |
| CH₂CH₃ | 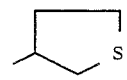 | 3-Cl |
| (CH₂)₂CH₃ | 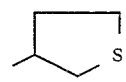 | 3-Cl |
| CH₂CH₃ | 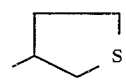 | H |
| (CH₂)₂CH₃ | 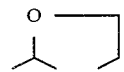 | H |
| CH₂CH₃ | 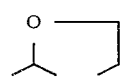 | 4-F |
| (CH₂)₂CH₃ | 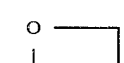 | 4-F |
| CH₂CH₃ | 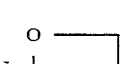 | 3-CH₃ |
| (CH₂)₂CH₃ | 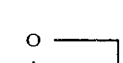 | 3-CH₃ |
| CH₂CH₃ | 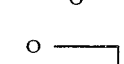 | 3-CF₃ |
| (CH₂)₂CH₃ | 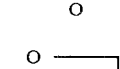 | 3-CF₃ |
| CH₂CH₃ | 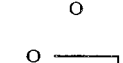 | 4-C(CH₃)₃ |
| (CH₂)₂CH₃ | 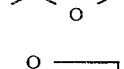 | 4-C(CH₃)₃ |
| CH₂CH₃ | 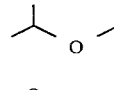 | 3-Cl |
| (CH₂)₂CH₃ | 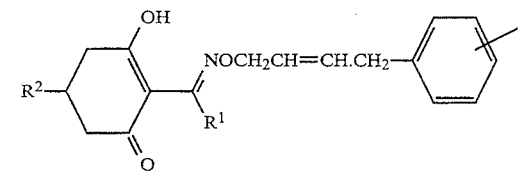 | 3-Cl |
| CH₂CH₃ | 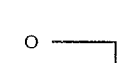 | H |
| (CH₂)₂CH₃ | 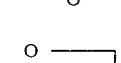 | H |
| CH₂CH₃ | 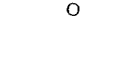 | 4-F |
| (CH₂)₂CH₃ | 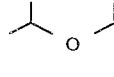 | 4-F |
| CH₂CH₃ | 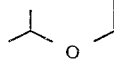 | 3-CH₃ |
| (CH₂)₂CH₃ | 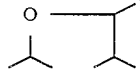 | 3-CH₃ |
| CH₂CH₃ | 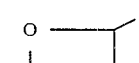 | 3-CF₃ |
| (CH₂)₂CH₃ | 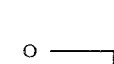 | 3-CF₃ |
| CH₂CH₃ | 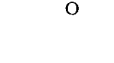 | 4-C(CH₃)₃ |
| (CH₂)₂CH₃ | 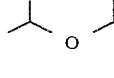 | 4-C(CH₃)₃ |

TABLE B-continued

Structure: cyclohexanedione with OH, R², R¹, N-O-CH₂-CH=CH-CH₂-phenyl(X)ₙ

| R¹ | R² | X |
|---|---|---|
| CH₂CH₃ | 2-isopropyl-4,5-dimethyl-1,3-dioxolane | 3-Cl |
| (CH₂)₂CH₃ | 2-isopropyl-4,5-dimethyl-1,3-dioxolane | 3-Cl |
| CH₂CH₃ | 2-isopropyl-1,3-dithiolane | H |
| (CH₂)₂CH₃ | 2-isopropyl-1,3-dithiolane | H |
| CH₂CH₃ | 2-isopropyl-1,3-dithiolane | 4-F |
| (CH₂)₂CH₃ | 2-isopropyl-1,3-dithiolane | 4-F |
| CH₂CH₃ | 2-isopropyl-1,3-dithiolane | 3-CH₃ |
| (CH₂)₂CH₃ | 2-isopropyl-1,3-dithiolane | 3-CH₃ |
| CH₂CH₃ | 2-isopropyl-1,3-dithiolane | 3-CF₃ |
| (CH₂)₂CH₃ | 2-isopropyl-1,3-dithiolane | 3-CF₃ |
| CH₂CH₃ | 2-isopropyl-1,3-dithiolane | 4-C(CH₃)₃ |
| (CH₂)₂CH₃ | 2-isopropyl-1,3-dithiolane | 4-C(CH₃)₃ |
| CH₂CH₃ | 2-isopropyl-1,3-dithiolane | 3-Cl |
| (CH₂)₂CH₃ | 2-isopropyl-1,3-dithiolane | 3-Cl |
| CH₂CH₃ | 3,6-dihydro-2H-pyran-4-yl | H |
| (CH₂)₂CH₃ | 3,6-dihydro-2H-pyran-4-yl | H |
| CH₂CH₃ | 3,6-dihydro-2H-pyran-4-yl | 4-F |
| (CH₂)₂CH₃ | 3,6-dihydro-2H-pyran-4-yl | 4-F |
| CH₂CH₃ | 3,6-dihydro-2H-pyran-4-yl | 3-CH₃ |
| (CH₂)₂CH₃ | 3,6-dihydro-2H-pyran-4-yl | 3-CH₃ |
| CH₂CH₃ | 3,6-dihydro-2H-pyran-4-yl | 3-CF₃ |
| (CH₂)₂CH₃ | 3,6-dihydro-2H-pyran-4-yl | 3-CF₃ |
| CH₂CH₃ | 3,6-dihydro-2H-pyran-4-yl | 4-C(CH₃)₃ |
| (CH₂)₂CH₃ | 3,6-dihydro-2H-pyran-4-yl | 4-C(CH₃)₃ |

TABLE B-continued

[Structure: cyclohexane-dione with OH, R², and C(R¹)=N-OCH₂CH=CH.CH₂-phenyl-(X)ₙ]

| R¹ | R² | X |
|---|---|---|
| CH₂CH₃ | 3,6-dihydro-2H-pyran-4-yl | 3-Cl |
| (CH₂)₂CH₃ | 3,6-dihydro-2H-pyran-4-yl | 3-Cl |
| CH₂CH₃ | 3,4-dibromotetrahydropyran-3-yl | H |
| (CH₂)₂CH₃ | 3,4-dibromotetrahydropyran-3-yl | H |
| CH₂CH₃ | 3,4-dibromotetrahydropyran-3-yl | 4-F |
| (CH₂)₂CH₃ | 3,4-dibromotetrahydropyran-3-yl | 4-F |
| CH₂CH₃ | 3,4-dibromotetrahydropyran-3-yl | 3-CH₃ |
| (CH₂)₂CH₃ | 3,4-dibromotetrahydropyran-3-yl | 3-CH₃ |
| CH₂CH₃ | 3,4-dibromotetrahydropyran-3-yl | 3-CF₃ |
| (CH₂)₂CH₃ | 3,4-dibromotetrahydropyran-3-yl | 3-CF₃ |
| CH₂CH₃ | 3,4-dibromotetrahydropyran-3-yl | 4-C(CH₃)₃ |
| (CH₂)₂CH₃ | 3,4-dibromotetrahydropyran-3-yl | 4-C(CH₃)₃ |
| CH₂CH₃ | 3,4-dibromotetrahydropyran-3-yl | 3-Cl |
| (CH₂)₂CH₃ | 3,4-dibromotetrahydropyran-3-yl | 3-Cl |
| CH₂CH₃ | isothiazol-3-yl | H |
| (CH₂)₂CH₃ | isothiazol-3-yl | H |
| CH₂CH₃ | isothiazol-3-yl | 4-F |
| (CH₂)₂CH₃ | isothiazol-3-yl | 4-F |
| CH₂CH₃ | isothiazol-3-yl | 3-CH₃ |
| (CH₂)₂CH₃ | isothiazol-3-yl | 3-CH₃ |
| CH₂CH₃ | isothiazol-3-yl | 3-CF₃ |
| (CH₂)₂CH₃ | isothiazol-3-yl | 3-CF₃ |

TABLE B-continued

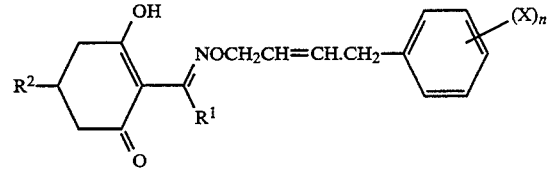

| R¹ | R² | X |
|---|---|---|
| CH$_2$CH$_3$ | 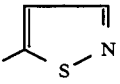 | 4-C(CH$_3$)$_3$ |
| (CH$_2$)$_2$CH$_3$ | 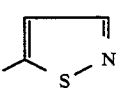 | 4-C(CH$_3$)$_3$ |
| CH$_2$CH$_3$ | 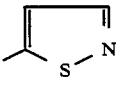 | 3-Cl |
| (CH$_2$)$_2$CH$_3$ | 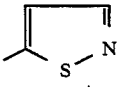 | 3-Cl |
| CH$_2$CH$_3$ | 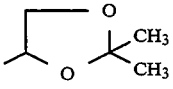 | 3-CF$_3$ |
| (CH$_2$)$_2$CH$_3$ | 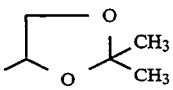 | 3-CF$_3$ |
| CH$_2$CH$_3$ | 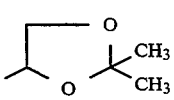 | 4-C(CH$_3$)$_3$ |
| (CH$_2$)$_2$CH$_3$ | 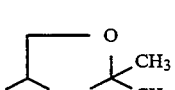 | 4-C(CH$_3$)$_3$ |
| CH$_2$CH$_3$ | 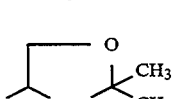 | H |
| (CH$_2$)$_2$CH$_3$ | 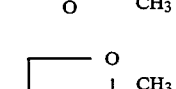 | H |
| CH$_2$CH$_3$ | 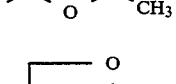 | H |
| (CH$_2$)$_2$CH$_3$ | 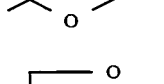 | H |
| CH$_2$CH$_3$ | 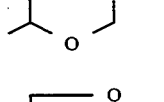 | 3-CF$_3$ |
| (CH$_2$)$_2$CH$_3$ | 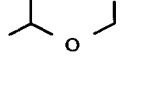 | 3-CF$_3$ |
| CH$_2$CH$_3$ |  | 4-C(CH$_3$)$_3$ |
| (CH$_2$)$_2$CH$_3$ | 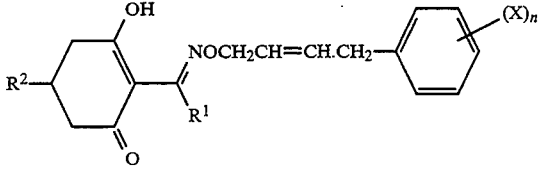 | 4-C(CH$_3$)$_3$ |
| CH$_2$CH$_3$ | 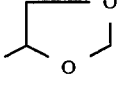 | H |
| (CH$_2$)$_2$CH$_3$ | 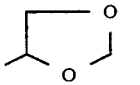 | H |
| CH$_2$CH$_3$ | 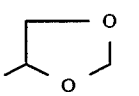 | 3-CF$_3$ |
| (CH$_2$)$_2$CH$_3$ |  | 3-CF$_3$ |
| CH$_2$CH$_3$ | 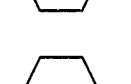 | 4-C(CH$_3$)$_3$ |
| (CH$_2$)$_2$CH$_3$ |  | 4-C(CH$_3$)$_3$ |
| CH$_2$CH$_3$ | 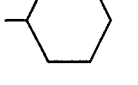 | H |
| (CH$_2$)$_2$CH$_3$ | 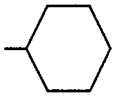 | H |
| CH$_2$CH$_3$ | 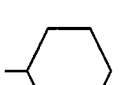 | 3-CF$_3$ |

TABLE B-continued

Structure: cyclohexenone with OH, R² substituent, =N-OCH₂CH=CH.CH₂-phenyl(X)ₙ, R¹ group, and =O.

| R¹ | R² | X |
|---|---|---|
| (CH₂)₂CH₃ | cyclohexenyl | 3-CF₃ |
| CH₂CH₃ | cyclohexenyl | 4-C(CH₃)₃ |
| (CH₂)₂CH₃ | cyclohexenyl | 4-C(CH₃)₃ |

The cyclohexenone derivatives I, and herbicidal agents containing them, may be applied for instance in the form of directly sprayable solutions, powders, suspensions (including high-percentage aqueous, oily or other suspensions), dispersions, emulsions, otl dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel otl, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, cyclohexanol, cyclohexanone, chlorobenzene, isophorone, etc., and strongly polar solvents such as N,N-dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of aromatic sulfonic acids, e.g., ligntnsulfonic acid, phenolsulfontc acid, naphthalenesulfonic acid and dibutylnaphthalenesulfonic acid, and of fatty acids, alkyl and alkylaryl sulfonates, and alkyl, lauryl ether and fatty alcohol sulfates, alkali metal and alkaline earth metal salts of dibutyl-naphthalenesulfonic acid, tauryl ether sulfate, fatty alcohol sulfates, and salts of sulfated hexadecanols, heptadecanols, and octadecanols, salts of fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, tsotrtdecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain meals, bark meal, wood meal, and nutshell meal, cellulosic powders, etc.

The formulations contain from 0.1 to 95, and preferably 0.5 to 90, % by weight of active ingredient. The active ingredients are used in a purity of from 90 to 100, and preferably from 95 to 100, % (according to the NMR spectrum).

The compounds I according to the invention may be formulated for example as follows.

I. 90 parts by weight of compound no. 1.11 is mixed with 10 parts by weight of N-methyl-alpha-pyrrolidone. A mixture is obtained which is suitable for application in the form of very fine drops.

II. 20 parts by weight of compound no. 2.3 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 3.31 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 3.46 is dissolved in a mixture consisting of 25 parts by weight of cyclohexanone, 65 parts by weight of a mineral oil fraction having a boiling point between 210° and 280° C., and 10 parts by weight of the adduct of 40 moles of ethylene oxide and 1 mole of castor otl. By pouring the solution into 100,000 parts by weight of water and uniformly distributing it therein, an aqueous dispersion is obtained containing 0.02% by weight of the active ingredient.

V. 20 parts by weight of compound no. 4.5 is well mixed with 3 parts by weight of the sodium salt of diisobutylnaphthalene-alpha-sulfonic acid, 17 parts by. weight of the sodium. salt of a ltgnin-sulfonic acid obtained from a sulfite waste liquor, and 60 parts by weight of powdered silica gel, and triturated in a hamer mill. By uniformly distributing the mixture in 20,000 parts by weight of water, a spray liquor is obtained containing 0.1% by weight of the active ingredient.

VI. 3 parts by weight of compound no. 5.2 is intimately mixed with 97 parts by weight of particulate kaolin. A dust is obtained containing 3% by weight of the active ingredient.

VII. 30 parts by weight of compound no. 6.8 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts by weight of compound no. 7.3 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The active ingredients or the herbicidal agents containing them may be applied pre- or postemergence. if certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The application rates depend on the objective to be achieved, the time of the year, the plants to be combated and their growth stage, and are from 0.01 to 3.0, preferably 0.05 to 1.0, kg of active ingredient per hectare.

In view of the number of weeds that can be combated, the tolerance by crop plants or the desired influence on their growth, and in view of the number of application methods possible, the compounds according to the invention, or agents containing them, may be used in a further large number of crops for removing unwanted plants. The following crops are given by way of example:

| Botanical name | Common name |
| --- | --- |
| Allium cepa | onions |
| Ananas comosus | pineapples |
| Arachis hypogaea | peanuts (groundnuts) |
| Asparagus officinalis | asparagus |
| Avena sativa | oats |
| Beta vulgaris spp. altissima | sugarbeets |
| Beta vulgaris spp. rapa | fodder beets |
| Beta vulgaris spp. esculenta | table beets, red beets |
| Brassica napus var. napus | rapeseed |
| Brassica napus var. napobrassica | swedes |
| Brassica napus var. rapa | turnips |
| Brassica rapa var. silvestris | |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | mandarins |
| Citrus sinensis | orange trees |
| Coffea arabica (Coffea canephora, Coffea liberica) | coffee plants |
| Cucumis melo | melons |
| Cucumis sativus | cucumbers |
| Cynodon dactylon | Bermudagrass |
| Daucus carota | carrots |
| Elais guineensis | oil palms |
| Fragaria vesca | strawberries |
| Glycine max | soybeans |
| Gossypium hirsutum (Gossypium arboreum, Gossypium herbaceum, Gossypium vitifolium) | cotton |
| Helianthus annuus | sunflowers |
| Helianthus tuberosus | Jerusalem artichoke |
| Hevea brasiliensis | rubber plants |
| Hordeum vulgare | barley |
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicotiana tabacum (N. rustica) | tobacco |
| Olea europaea | olive trees |
| Oryza sativa | rice |
| Panicum miliaceum | millet |
| Phaseolus lunatus | limabeans |
| Phaseolus mungo | mungbeans |
| Phaseolus vulgaris | snapbeans, green beans, dry beans |
| Pennisetum glaucum | pearl millet |
| Petroselinum crispum spp. tuberosum | parsley |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Sorghum bicolor (s. vulgare) | sorghum |
| Sorghum dochna | sorgo |
| Spinacia oleracea | spinach |
| Theobroma cacao | cacao plants |
| Trifolium pratense | red clover |
| Triticum aestivum | wheat |
| Triticum durum | durum wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, sweet corn, maize |

To increase the spectrum of action and to achieve synergistic effects, the cyclohexenone derivatives of the formula I may be mixed and applied together with numerous representatives of other herbicidal or growth-regulating active ingredient groups. Examples of suitable components are diazines, 4H-3,1-benzoxazine derivatives, benzothiadiazinones, 2,6-dinitroanilines, N- phenylcarbamates, thiolcarbamates, halocarboxylic acids, triazines, amides, ureas, diphenyl ethers, triazinones, uracils, benzofuran derivatives, cyclohexane-1,3-dione derivatives, quinolthecarboxylic acids, cyclohexenones, (hetero)-aryloxypropionic acids and salts, esters and amides thereof, etc.

It may also be useful to apply the cyclohexenone derivatives of the formula I, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxtc oils and oil concentrates may also be added.

The directions given in the synthesis examples below were used, after appropriate modifications of the starting materials, to obtain further compounds of the formula I. The compounds thus obtained are listed with physical data in the tables below. Compounds without these data may be obtained analogously. In view of their close structural relationship to the compounds manufactured and investigated, they are expected to have a similar action.

SYNTHESIS EXAMPLE

Manufacturing directions for Example 3.2 a) At 0° C., 69.1 g (1 moll of sodium nitrite in 100 ml of water is introduced into a solution of 93.1 g (1 moll of aniline in 340 ml of water and 225 ml of concentrated hydrochloric acid.

b) At −15° C., 67.6 g (1.25 moll of butadiene is gassed into 840 ml of acetone and 50 ml of water; 15.5 g of copper(II) chloride and 22.5 g of calcium oxide are introduced, and the diazonium salt solution prepared in a) is added over a 2-hour period. This reaction mixture is allowed to heat up to 25° C. After the mixture has been stirred for 6 hours, it is extracted with methyl tert-butyl ether, and the organic extract is evaporated down and distilled in a thin-film evaporator (0.2 mm Hg; 80° C.). A mixture of 1-chloro-4-phenylbut-2-ene and 3-chloro-4-phenylbut-1-ene (78:22) is obtained in a total yield of 55%.

c) 78.3 g (0.48 mol) of N-hydroxyphthalimide and then 44.2 g (0.32 mol) of potassium carbonate are added to 480 ml of anhydrous N-methylpyrrolidone. At an internal temperature of 40° C., 88.8 g (0.54 mol) of the chloride mixture obtained under b) is dripped in. The mixture is heated to 60° C. and stirred for a further 6 hours. After the mixture has cooled it is poured into 2 liters of ice water and then filtered. Washing and drying give 90% of theory of (E)-N-(4-phenyl-2-butenyloxy)-phthalimide. Melting point: 70°–71° C. (isopropanol).

d) At 60° C. and while stirring, 11.6 g (0.19 mol) of ethanolamine is added to 55.5 g (0.19 mol) of the phthattmtde ether c) in 190 ml of ethyl acetate. After 5 hours, the precipitated N-(hydroxyethyl)-phthalimide is filtered off and 18.8 g of oxalic acid in 30 ml of ethyl acetate is added to the filtrate. There is obtained 95% of theory of (E)-4-phenyl-2-butenyloxyamine as the oxalate salt. Melting point: 127°–129° C.

e) 4.3 g (0.016 mol) of 2-propionyl-5-(3-tetrahydrothiopyranyl)-cyclohexane-1,3-dione, 4.5 g (0.018 mol) of 4-phenylbut-2-enyloxyammonium oxalate and 3.0 g of sodium bicarbonate are stirred in 100 ml of methanol for 16 hours at 25° C. The solvent is distilled off under reduced pressure and the residue is chromatographed on silica gel with a mixture of toluene and ethyl acetate (8:2 volume ratio). After removal of the solvent there is obtained 2.2 g (33.3% of theory) of 2-[1-(4-phenylbut-2-enyloximtno)-propyl]-5-(3-tetrahydrothtopyranyl)-cyclohex-2-en-1-one as a resin.

Where the tables give no indication of the contrary, the alkenyl radicals are present in the E configuration.

TABLE 1

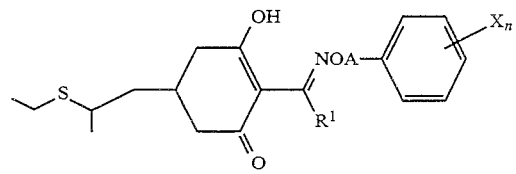

| No. | R¹ | A | X | n | Phys. data [mp (°C.); NMR* (δ in ppm)] |
|---|---|---|---|---|---|
| 1.1 | propyl | but-2-enylene | — | 0 | 4.5(d, 2H); 5.6–6.1(m, 2H) |
| 1.2 | propyl | but-2-enylene | 4-t-butyl | 1 | 4.5(d, 2H); 5.6–6.0(m, 2H); 1.3(s, 9H) |
| 1.3 | propyl | but-2-enylene | 4-trifluoromethyl | 1 | 4.5(d, 2H); 5.6–6.0(m, 2H) |
| 1.4 | propyl | but-2-enylene | 4-fluorine | 1 | 4.5(d, 2H); 5.6–6.0(m, 2H) |
| 1.5 | propyl | but-2-enylene | 4-chlorine | 1 | 4.5(d, 2H); 5.6–6.0(m, 2H) |
| 1.6 | propyl | butylene | — | 0 | 1.0(s); 4.0–4.2(m); 7.1–7.4(m) |
| 1.7 | ethyl | but-2-enylene | — | 0 | 4.5(d, 2H); 5.6–6.0(m, 2H) |
| 1.8 | propyl | but-2-enylene | 3-chlorine | 1 | 4.5(d, 2H); 5.6–6.0(m, 2H) |
| 1.9 | propyl | but-3-enylene | 4-chlorine | 1 | 4.1(t, 2H); 6.0–6.5(m, 2H) |
| 1.10 | propyl | but-3-enylene | 4-methyl | 1 | 2.3(s, 3H); 4.1(t, 2H); 6.0–6.5(m, 2H) |
| 1.11 | propyl | but-3-enylene | 4-fluorine | 1 | 4.1(t, 2H); 6.0–6.5(m, 2H) |
| 1.12 | propyl | but-3-enylene | — | 0 | 4.1(t, 2H); 6.0–6.6(m, 2H) |
| 1.13 | propyl | but-2-enylene | 4-methoxy | 1 | 3.8(s, 3H); 4.4(d, 2H); 5.5–6.0(m, 2H) |
| 1.14 | propyl | but-2-enylene | 4-methyl | 1 | 4.5(d, 2H); 5.6–6.0(m, 2H) |

*selected signals

TABLE 2

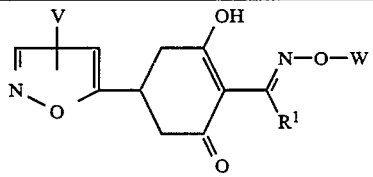

| No. | R¹ | V | W | Phys. data [mp. (°C.); NMR* (δ in ppm)] |
|---|---|---|---|---|
| 2.1 | ethyl | 3-ethyl | 4-phenyl-but-2-enyl | 58-59 |
| 2.2 | propyl | 3-ethyl | 4-phenyl-but-2-enyl | 4.5(d, 2H), 5.6-6.1(m, 2H) |
| 2.3 | ethyl | 3-isopropyl | 4-phenyl-but-2-enyl | 57-58 |
| 2.4 | ethyl | 3-(1-methoxyethyl) | 4-phenyl-but-2-enyl | 3.3(s, 3H), 5.6-6.1(m, 2H) |

TABLE 3

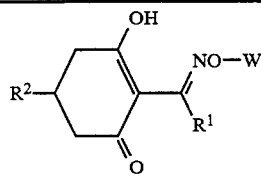

| No. | R¹ | R² | W | Phys. data [mp (°C.); NMR* (δ in ppm)] |
|---|---|---|---|---|
| 3.1 | propyl | tetrahydrothiopyran-3-yl | 4-phenyl-but-2-enyl | 4.5(d, 2H); 5.5-6.1(m, 2H) |
| 3.2 | ethyl | tetrahydrothiopyran-3-yl | 4-phenyl-but-2-enyl | 4.5(d, 2H); 5.6-6.1(m, 2H) |
| 3.3 | propyl | tetrahydrothiopyran-3-yl | 4-(4-fluorophenyl)-but-2-enyl | 4.5(d, 2H); 5.6-6.0(m, 2H) |
| 3.4 | propyl | tetrahydrothiopyran-3-yl | 4-(4-chlorophenyl)-but-2-enyl | 4.5(d, 2H); 5.6-6.0(m, 2H) |
| 3.5 | propyl | tetrahydrothiopyran-3-yl | 4-(4-trifluoromethylphenyl)-but-2-enyl | 4.5(d, 2H); 5.6-6.0(m, 2H) |
| 3.6 | propyl | tetrahydrothiopyran-3-yl | 4-(4-t-butylphenyl)-but-2-enyl | 4.5(d, 2H); 5.6-6.1(m, 2H); 1.3(s, 9H) |
| 3.7 | ethyl | tetrahydrothiopyran-3-yl | 4-(4-fluorophenyl)-but-2-enyl | 4.5(d, 2H); 5.6-6.0(m, 2H) |
| 3.8 | ethyl | tetrahydrothiopyran-3-yl | 4-(4-chlorophenyl)-but-2-enyl | 4.5(d, 2H); 5.6-6.0(m, 2H) |
| 3.9 | ethyl | tetrahydrothiopyran-3-yl | 4-(4-t-butylphenyl)-but-2-enyl | 4.5(d, 2H); 5.6-6.0(m, 2H); 1.3(s, 9H) |
| 3.10 | ethyl | tetrahydrothiopyran-3-yl | 4-(4-trifluoromethylphenyl)-but-2-enyl | 4.5(d, 2H); 5.6-6.0(m, 2H) |
| 3.11 | methyl | tetrahydrothiopyran-3-yl | 4-phenyl-but-2-enyl | 4.5(d, 2H); 5.6-6.0(m, 2H); 2.4(s, 3H) |
| 3.12 | ethyl | tetrahydropyran-4-yl | 4-phenyl-but-2-enyl | 62-64 |
| 3.13 | ethyl | tetrahydropyran-4-yl | 4-(4-fluorophenyl)-but-2-enyl | 4.5(d, 2H); 5.6-6.0(m, 2H) |
| 3.14 | ethyl | tetrahydropyran-4-yl | 4-(4-chlorophenyl)-but-2-enyl | 4.5(d, 2H); 5.6-6.0(m, 2H) |
| 3.15 | ethyl | tetrahydropyran-4-yl | 4-(4-t-butylphenyl)-but-2-enyl | 99-101 |
| 3.16 | ethyl | tetrahydropyran-4-yl | 4-(4-trifluoromethylphenyl)-but-2-enyl | 4.5(d, 2H), 5.6-6.0(m, 2H) |
| 3.17 | propyl | tetrahydropyran-4-yl | 4-phenyl-but-2-enyl | 4.5(d, 2H); 5.6-6.1(m, 2H) |
| 3.18 | propyl | tetrahydropyran-4-yl | 4-(4-fluorophenyl)-but-2-enyl | 4.5(d, 2H); 5.6-6.0(m, 2H) |
| 3.19 | propyl | tetrahydropyran-4-yl | 4-(4-chlorophenyl)-but-2-enyl | 4.5(d, 2H); 5.6-6.0(m, 2H) |
| 3.20 | propyl | tetrahydropyran-4-yl | 4-(4-t-butylphenyl)-but-2-enyl | 84-86 |
| 3.21 | propyl | tetrahydropyran-4-yl | 4-(4-trifluoromethylphenyl)-but-2-enyl | 4.5(d, 2H); 5.6-6.0(m, 2H) |
| 3.22 | ethyl | tetrahydropyran-3-yl | 4-phenyl-but-2-enyl | 4.5(d, 2H); 5.6-6.0(m, 2H) |
| 3.23 | ethyl | tetrahydropyran-3-yl | 4-(4-fluorophenyl)-but-2-enyl | 4.5(d, 2H); 5.6-6.0(m, 2H) |
| 3.24 | ethyl | tetrahydropyran-3-yl | 4-(4-chlorophenyl)-but-2-enyl | 4.5(d, 2H); 5.6-6.0(m, 2H) |
| 3.25 | ethyl | tetrahydropyran-3-yl | 4-(4-t-butylphenyl)-but-2-enyl | 4.5(d, 2H); 5.6-6.0(m, 2H); 1.3(s, 9H) |
| 3.26 | ethyl | tetrahydropyran-3-yl | 4-(4-trifluoromethylphenyl)-but-2-enyl | 4.5(d, 2H); 5.6-6.1(m, 2H) |
| 3.27 | propyl | tetrahydropyran-3-yl | 4-phenyl-but-2-enyl | 4.5(d, 2H); 5.6-6.0(m, 2H) |
| 3.28 | propyl | tetrahydropyran-3-yl | 4-(4-fluorophenyl)-but-2-enyl | 4.5(d, 2H); 5.6-6.0(m, 2H) |
| 3.29 | propyl | tetrahydropyran-3-yl | 4-(4-chlorophenyl)-but-2-enyl | 4.5(d, 2H); 5.6-6.0(m, 2H) |
| 3.30 | propyl | tetrahydropyran-3-yl | 4-(4-t-butylphenyl)-but-2-enyl | 4.5(d, 2H); 5.6-6.0(m, 2H); 1.3(s, 9H) |
| 3.31 | propyl | tetrahydropyran-3-yl | 4-(4-trifluoromethylphenyl)-but-2-enyl | 4.5(d, 2H); 5.6-6.0(m, 2H) |
| 3.32 | ethyl | tetrahydrothiopyran-3-yl | 4-(3-chlorophenyl)-but-2-enyl | 4.5(d, 2H); 5.6-6.0(m, 2H) |
| 3.33 | ethyl | tetrahydrothiopyran-3-yl | 4-(4-methylphenyl)-but-2-enyl | 2.3(s, 3H); 4.5(d, 2H); 5.6-6.0(m, 2H) |
| 3.34 | ethyl | tetrahydrothiopyran-3-yl | 4-(4-chlorophenyl)-but-3-enyl | 4.2(t, 2H); 6.1-6.5(m, 2H) |
| 3.35 | ethyl | tetrahydrothiopyran-3-yl | 4-(4-methylphenyl)-but-3-enyl | 2.3(s, 3H); 4.2(t, 2H); 6.0-6.5(m, 2H) |
| 3.36 | ethyl | tetrahydrothiopyran-3-yl | 4-(4-fluorophenyl)-but-3-enyl | 4.2(t, 2H); 6.0-6.5(m, 2H) |
| 3.37 | ethyl | tetrahydrothiopyran-3-yl | 4-phenylbut-3-enyl | 4.2(t, 2H); 6.1-6.6(m, 2H) |
| 3.38 | propyl | tetrahydrothiopyran-3-yl | 4-phenylbut-3-enyl | 4.2(t, 2H); 6.1-6.6(m, 2H) |
| 3.39 | ethyl | tetrahydropyran-3-yl | 4-(3-chlorophenyl)-but-2-enyl | 4.5(d, 2H); 5.6-6.0(m, 2H) |
| 3.40 | ethyl | tetrahydropyran-3-yl | 4-phenylbut-3-enyl | 4.2(t, 2H); 6.1-6.6(m, 2H) |
| 3.41 | propyl | tetrahydropyran-3-yl | 4-phenylbut-3-enyl | 4.2(t, 2H); 6.0-6.6(m, 2H) |

TABLE 3-continued

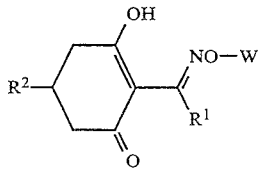

| No. | R¹ | R² | W | Phys. data [mp (°C.); NMR* (δ in ppm)] |
|---|---|---|---|---|
| 3.42 | ethyl | tetrahydropyran-4-yl | 4-phenylbut-3-enyl | 4.2(t, 2H); 6.1–6.6(m, 2H) |
| 3.43 | propyl | tetrahydropyran-4-yl | 4-phenylbut-3-enyl | 4.2(t, 2H); 6.1–6.6(m, 2H) |
| 3.44 | propyl | 3,4-dibromotetrahydro-thiopyran-3-yl | 4-(4-trifluoromethylphenyl)-but-2-enyl | 3.5(d, 2H); 7.55(d, 2H) |
| 3.45 | propyl | 3,4-dibromotetrahydro-pyran-3-yl | 4-(4-fluorophenyl)-but-3-enyl | 4.15(t, 2H); 5.9–6.2(m, 1H); 6.4(d, 1H) |
| 3.46 | propyl | 3,4-dibromotetrahydro-pyran-3-yl | 4-(4-fluorophenyl)-but-2-enyl | 4.49(d, 2H); 5.5–6.1(m, 2H) |
| 3.47 | propyl | 3,4-dibromotetrahydro-pyran-3-yl | 4-(4-t.-butylphenyl)-but-2-enyl | 4.49(d, 2H); 5.55–6.1(m, 2H) |
| 3.48 | propyl | 3,4-dibromotetrahydro-pyran-3-yl | 4-(4-methylphenyl)-but-2-enyl | 4.49(d, 2H); 5.55–6.1(m, 2H) |
| 3.49 | propyl | 3,4-dibromotetrahydro-pyran-3-yl | 4-(4-trifluoromethylphenyl)-but-2-enyl | 4.52(s, 2H); 5.5–6.1(m, 2H) |
| 3.50 | propyl | 3,4-dibromotetrahydro-pyran-3-yl | 4-(3-chlorophenyl)-but-2-enyl | 4.5(d, 2H); 5.5–6.1(m, 2H) |
| 3.51 | propyl | 3,4-dibromotetrahydro-pyran-3-yl | 4-(4-methylphenyl)-but-3-enyl | 4.18(t, 2H); 6.0–6.2(m, 1H); 6.45(d, 1H) |
| 3.52 | propyl | 4-methylcyclohex-3-enyl | 4-(4-trifluoromethylphenyl)-but-2-enyl | 4.05(m, 2H); 5.5–6.1(m, 2H) |
| 3.53 | propyl | 4-methylcyclohex-3-enyl | 4-(4-fluoromethyl)-but-2-enyl | 4.5(d, 2H); 5.5–6.1(m, 2H) |
| 3.54 | propyl | tetrahydrothiopyran-3-yl | 4-(4-methoxyphenyl)but-2-enyl | 3.8(s, 3H); 4.4(d, 2H); 5.5–6.0(m, 2H) |
| 3.55 | ethyl | tetrahydrothiopyran-3-yl | 4-(4-methoxyphenyl)but-2-enyl | 3.8(s, 3H); 4.5(d, 2H); 5.6–6.0(m, 2H) |
| 3.56 | propyl | tetrahydropyran-3-yl | 4-(4-methoxyphenyl)but-2-enyl | 3.8(s, 3H); 4.5(d, 2H); 5.6–6.0(m, 2H) |
| 3.57 | ethyl | tetrahydropyran-3-yl | 4-(4-methoxyphenyl)but-2-enyl | 3.8(s, 3H); 4.5(d, 2H); 5.6–6.0(m, 2H) |
| 3.58 | propyl | tetrahydropyran-4-yl | 4-(4-methoxyphenyl)but-2-enyl | 3.8(s, 3H); 4.4(d, 2H); 5.5–6.0(m, 2H) |
| 3.59 | ethyl | tetrahydropyran-4-yl | 4-(4-methoxyphenyl)but-2-enyl | 3.8(s, 3H); 4.5(d, 2H); 5.5–6.0(m, 2H) |
| 3.60 | ethyl | tetrahydrothiopyran-3-yl | Z-4-phenylbut-2-enyl | 4.7(d, 2H); 5.8–6.0(m, 2H) |
| 3.61 | propyl | tetrahydrothiopyran-3-yl | Z-4-phenylbut-2-enyl | 4.7(d, 2H); 5.8–6.0(m, 2H) |
| 3.62 | propyl | tetrahydropyran-3-yl | Z-4-phenylbut-2-enyl | 4.7(d, 2H); 5.8–6.0(m, 2H) |
| 3.63 | propyl | tetrahydropyran-4-yl | Z-4-phenylbut-2-enyl | 4.7(d, 2H); 5.8–6.0(m, 2H) |
| 3.64 | ethyl | tetrahydropyran-4-yl | Z-4-phenylbut-2-enyl | 4.7(d, 2H); 5.8–6.0(m, 2H) |
| 3.65 | propyl | tetrahydrothiopyran-3-yl | 4-(4-methylphenyl)but-2-enyl | 2.3(s, 3H); 4.5(d, 2H); 5.6–6.0(m, 2H) |
| 3.66 | propyl | tetrahydrothiopyran-3-yl | 4-(3-chlorophenyl)but-2-enyl | 4.5(d, 2H); 5.6–6.0(m, 2H) |
| 3.67 | propyl | tetrahydrothiopyran-3-yl | 4-(3,4-dichlorophenyl)but-2-enyl | 4.5(d, 2H); 5.6–6.0(m, 2H) |
| 3.68 | ethyl | tetrahydrothiopyran-3-yl | 4-(3,4-dichlorophenyl)but-2-enyl | 4.5(d, 2H); 5.6–6.0(m, 2H) |
| 3.69 | propyl | tetrahydropyran-3-yl | 4-(3,4-dichlorophenyl)but-2-enyl | 4.5(d, 2H); 5.6–6.0(m, 2H) |
| 3.70 | propyl | tetrahydropyran-4-yl | 4-(3,4-dichlorophenyl)but-2-enyl | 4.5(d, 2H); 5.6–6.0(m, 2H) |
| 3.71 | propyl | tetrahydrothiopyran-3-yl | 4-(4-bromophenyl)but-3-enyl | 4.2(t, 2H); 6.2(dt, 1H); 6.4(d, 1H) |
| 3.72 | ethyl | tetrahydrothiopyran-3-yl | 4-(4-bromophenyl)but-3-enyl | 4.2(t, 2H); 6.2(dt, 1H); 6.4(d, 1H) |
| 3.73 | propyl | tetrahydrothiopyran-3-yl | 4-(4-fluorophenyl)but-3-enyl | 4.6(t, 2H); 6.1(dt, 1H); 6.6(d, 1H) |
| 3.74 | propyl | tetrahydrothiopyran-3-yl | 4-(4-chlorophenyl)but-3-enyl | 4.2(t, 2H); 6.1–6.5(2m, 2H) |
| 3.75 | propyl | tetrahydrothiopyran-3-yl | 4-(4-methylphenyl)but-3-enyl | 4.2(t, 2H); 6.1–6.2(m, 2H); 6.6(d, 1H) |
| 3.76 | propyl | tetrahydropyran-3-yl | 4-(4-bromophenyl)but-3-enyl | 4.2(t, 2H); 6.0–6.4(2m, 2H) |
| 3.77 | propyl | tetrahydropyran-4-yl | 4-(4-bromophenyl)but-3-enyl | 4.2(t, 2H); 6.0–6.5(2m, 2H) |
| 3.78 | ethyl | tetrahydropyran-4-yl | 4-(4-bromophenyl)but-3-enyl | 4.2(t, 2H); 6.0–6.5(2m, 2H) |

TABLE 4

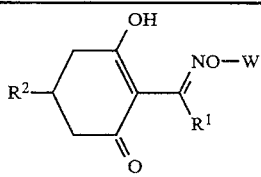

| No. | R¹ | R² | W | Phys. data [mp (°C.); NMR* (δ in ppm)] |
|---|---|---|---|---|
| 4.1 | ethyl | phenyl | 4-phenyl-but-2-enyl | 4.5(d, 2H); 5.6–6.0(m, 2H) |
| 4.2 | propyl | phenyl | 4-phenyl-but-2-enyl | 4.5(d, 2H); 5.6–6.0(m, 2H) |
| 4.3 | ethyl | 4-trifluoromethylphenyl | 4-phenyl-but-2-enyl | 4.5(d, 2H); 5.6–6.1(m, 2H) |
| 4.4 | propyl | 4-trifluoromethylphenyl | 4-phenyl-but-2-enyl | 56–57 |
| 4.5 | ethyl | 4-ethylphenyl | 4-phenyl-but-2-enyl | 4.5(d, 2H); 5.6–6.1(m, 2H) |
| 4.6 | ethyl | 4-N-benzoylaminophenyl | 4-phenyl-but-2-enyl | 103–105 |
| 4.7 | propyl | 4-ethoxyphenyl | 4-phenyl-but-2-enyl | 4.6(d, 2H); 5.6–6.1(m, 2H) |
| 4.8 | propyl | 3-fluoro-4-(N-benzoylamino)phenyl | 4-phenyl-but-2-enyl | 87–90 |
| 4.9 | ethyl | 4-pyridyl | 4-phenyl-but-2-enyl | 4.5(d, 2H); 5.6–6.2(m, 2H) |

TABLE 4-continued

Structure: cyclohexenone with OH, R² substituent, and C(R¹)=N-O-W group

| No. | R¹ | R² | W | Phys. data [mp (°C.); NMR* (δ in ppm)] |
|---|---|---|---|---|
| 4.10 | propyl | 3-pyridyl | 4-phenyl-but-2-enyl | 4.6(d, 2H); 5.6–6.2(m, 2H) |
| 4.11 | ethyl | 4-(propynyl-3-oxy)phenyl | 4-phenyl-but-2-enyl | 4.6(d, 2H); 5.6–6.1(m, 2H) |
| 4.12 | propyl | 4-ethylphenyl | 4-phenyl-but-2-enyl | 4.5(d, 2H); 5.6–6.1(m, 2H) |

TABLE 5

Structure: cyclohexenone with OH, R² substituent, and C(R¹)=N-O-(CH₂)₄-phenyl-Xₙ group

| No. | R¹ | R² | Xₙ | Phys. data [mp (°C.); NMR* (δ in ppm)] |
|---|---|---|---|---|
| 5.1 | ethyl | tetrahydropyran-3-yl | H | 1.12(t); 7.1–7.4(m) |
| 5.2 | propyl | tetrahydropyran-4-yl | H | 0.99(t); 7.1–7.4(m) |
| 5.3 | methyl | tetrahydrothiopyran-3-yl | H | 2.31(s); 3.9–4.1(m); 7.1–7.35(m) |
| 5.4 | ethyl | tetrahydrothiopyran-3-yl | H | 1.1(t); 3.9–4.1(m); 7.1–7.4(m) |
| 5.5 | propyl | tetrahydrothiopyran-3-yl | H | 0.95(t); 3.9–4.1(m); 7.1–7.4(m) |
| 5.6 | propyl | 4-methylcyclohex-3-enyl | H | 4.5(d, 2H); 5.6–6.0(m, 2H) |
| 5.7 | methyl | tetrahydropyran-3-yl | H | |
| 5.8 | propyl | tetrahydropyran-3-yl | H | |
| 5.9 | methyl | tetrahydropyran-4-yl | H | |
| 5.10 | ethyl | tetrahydropyran-3-yl | 4-t-butyl | |
| 5.11 | propyl | tetrahydropyran-3-yl | 4-t-butyl | |
| 5.12 | ethyl | tetrahydrothiopyran-3-yl | 4-t-butyl | |
| 5.13 | propyl | tetrahydrothiopyran-3-yl | 4-t-butyl | |
| 5.14 | ethyl | tetrahydropyran-4-yl | 4-t-butyl | |
| 5.15 | propyl | tetrahydropyran-4-yl | 4-t-butyl | |
| 5.16 | ethyl | tetrahydropyran-3-yl | 4-CF₃ | |
| 5.17 | propyl | tetrahydropyran-3-yl | 4-CF₃ | |
| 5.18 | ethyl | tetrahydropyran-4-yl | 4-CF₃ | |
| 5.19 | propyl | tetrahydropyran-4-yl | 4-CF₃ | |
| 5.20 | ethyl | tetrahydrothiopyran-3-yl | 4-CF₃ | |
| 5.21 | propyl | tetrahydrothiopyran-3-yl | 4-CF₃ | |
| 5.22 | ethyl | tetrahydropyran-4-yl | H | |

TABLE 6

Structure: cyclohexenone with OH, R² substituent, and C(R¹)=N-O-W group

| No. | R¹ | R² | W | Phys. data [mp (°C.); NMR* (δ in ppm)] |
|---|---|---|---|---|
| 6.1 | ethyl | 3,4-dihydroxycyclohexyl | 4-(4-chlorophenyl)-but-2-enyl | 4.4–4.6(m, 2H); 5.5–6.0(m, 2H) |
| 6.2 | ethyl | 2-ethylthio-2-methylpropyl | 4-(4-fluorophenyl)-but-2-enyl | 1.3(s, 6H); 4.5(d, 2H); 5.6–6.0(m, 2H) |
| 6.3 | ethyl | 2-ethylthio-2-methylpropyl | 4-phenylbut-2-enyl | 1.3(s, 6H); 4.5(d, 2H); 5.5–6.1(m, 2H) |
| 6.4 | ethyl | 2-ethylthio-2-methylpropyl | 4-phenylbut-3-enyl | 1.3(s, 6H); 4.2(t, 2H); 6.2(dt, 1H); 6.4(dt, 1H) |
| 6.5 | ethyl | 2-ethylthio-2-methylpropyl | 4-(4-fluorophenyl)-but-3-enyl | 1.3(s, 6H); 4.2(t, 2H); 6.1(dt, 1H); 6.4(dt, 1H) |
| 6.6 | ethyl | 2-ethylthio-2-methylpropyl | 4-(4-chlorophenyl)-but-3-enyl | 1.3(s, 6H); 4.2(t, 2H); 6.2(dt, 1H); 6.5(dt, 1H) |
| 6.7 | ethyl | 2,6,6-trimethylcyclohexy-1-enyl | 4-phenylbut-2-enyl | 1.0(s, 6H); 4.5(d, 2H); 5.8–6.2(m, 2H) |
| 6.8 | propyl | 2,6,6-trimethylcyclohexy-1-enyl | 4-phenylbut-2-enyl | 1.0(s, 6H); 4.5(d, 2H); 5.6–6.1(m, 2H) |

TABLE 7

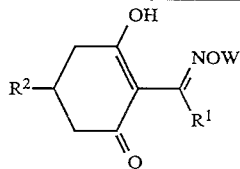

| No. | $R^1$ | $R^2$ | W | Phys. data [mp (°C.); NMR* (δ in ppm)] |
|---|---|---|---|---|
| 7.1 | propyl | tetrahydrothiopyran-3-yl | 4-(4-fluorophenyl)-pent-3-enyl | 2.0(s, 3H); 4.1(t, 2H); 5.7(t, 1H) |
| 7.2 | ethyl | tetrahydrothiopyran-3-yl | 4-(4-fluorophenyl)-pent-3-enyl | 2.0(s, 3H); 4.1(t, 2H); 5.7(t, 1H) |
| 7.3 | propyl | tetrahydropyran-3-yl | 4-(4-fluorophenyl)-pent-3-enyl | 2.0(s, 3H); 4.1(t, 2H); 5.7(t, 1H) |
| 7.4 | propyl | tetrahydropyran-4-yl | 4-(4-fluorophenyl)-pent-3-enyl | 2.0(s, 3H); 4.1(t, 2H); 5.7(t, 1H) |
| 7.5 | ethyl | tetrahydropyran-4-yl | 4-(4-fluorophenyl)-pent-3-enyl | 2.0(s, 3H); 4.1(t, 2H); 5.7(t, 1H) |

Use Examples

The action of the cyclohexenone derivatives of the formula I on the growth of plants is demonstrated by the following greenhouse experiments.

The vessels employed were plastic flowerpots having a volume of 300 cm³ and filled with a sandy loam containing about 3.0% humus. The seeds of the test plants were sown separately, according to species.

For the preemergence treatment, the formulated active ingredients were applied to the surface of the sotl immediately after the seeds had been sown. The compounds were emulsified or suspended in water as vehicle, and sprayed through finely distributing nozzles.

After the agents had been applied, the vessels were lightly sprinkler-irrigated to induce germination and growth. Transparent plastic covers were then placed on the vessels until the plants had taken root. The cover ensured uniform germination of the plants, insofar as this was not impaired by the active ingredients. The application rate in this treatment method was 0.5 kg/ha.

For the postemergence treatment, the plants were grown, depending on growth form, to a height of 3 to 15 cm before being treated with the compounds suspended or emulsified in water. The application rates for postemergence treatment were 0.06, 0.125 and 0.25 kg/ha.

The plants were kept in the greenhouse in accordance with their specific requirements. The experiments were run for from 2 to 4 weeks. During this period the plants were tended and their reactions to the various treatments assessed. The assessment scale was 0 to 100, 100 denoting nonemergence or complete destruction of at least the visible plant parts, and 0 denoting no damage or normal growth.

The plants employed for the experiments were Digitaria sanguinalis, Echtnochloa crus-galli, Leptochloa fascicularis, Medicago sativa, Oryza sativa, Setaria faberit, Setaria ttalica and Setaria viridis.

For combating unwanted grassy plants, for example compounds nos. 3.3, 3.4, 3.8, 3.13, 3.34, 3.36 and 3.73, applied postemergence at rates of 0.06, 0.125 and 0.25 kg/ha, proved to be suitable and were well tolerated by rice and alfalfa.

We claim:

1. A cyclohexenone oxime ether of the formula I

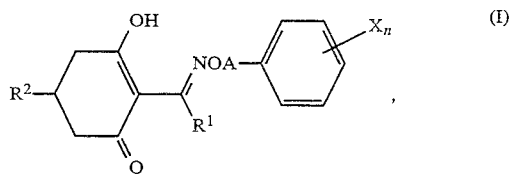

where $R^1$ is $C_1-C_6$-alkyl, A is a $C_4$-alkylene or $C_4$-alkenylene chain and these chains are optionally substituted by from one to three $C_1-C_3$-alkyl groups or halogen atoms, X is nitro, cyano, halogen, $C_1-C_4$-alkyl, $C_1-C_4$-alkoxy, $C_1-C_4$-alkylthio, $C_1-C_4$-haloalkyl, $C_1-C_4$-haloalkoxy, carboxyl, $C_1-C_4$-alkoxycarbonyl, benzyloxycarbonyl or phenyl, and said aromatic radicals are unsubstituted or optionally substituted by from one to three of the following substituents: nitro, cyano, halogen, $C_1-C_4$-alkyl, $C_1-C_4$-alkoxy, $C_1-C_4$-alkylthio, $C_1-C_4$-haloalkyl, $C_1-C_4$-haloalkyloxy, carboxyl, $C_1-C_4$-alkoxycarbonyl or benzyloxycarbonyl, n is from 0 to 3 or from 1 to 5 when X is halogen, $R^2$ is $C_1-C_4$-alkoxy-$C_1-C_4$-alkyl- or $C_1-C_4$-alkylthio-$C_1-C_6$-alkyl, $C_3-C_7$-cycloalkyl or $C_5-C_7$-cycloalkenyl, and these cyclic groups are unsubstituted or optionally substituted by from one to three of the following substituents: $C_1-C_4$-alkyl, $C_1-C_4$-alkoxy, $C_1-C_4$-alkylthio, $C_1-C_4$-haloalkyl, hydroxy or halogen; phenyl or pyridyl and these groups are unsubstituted or optionally substituted by from one to three of the following substituents: halogen, nitro, cyano, $C_1-C_4$-alkyl, $C_1-C_4$-alkoxy, $C_1-C_4$-alkylthio, $C_1-C_4$-haloalkyl, $C_3-C_6$-alkenyloxy, $C_3-C_6$-alkynyloxy or —$NR^3R^4$, where $R^3$ is hydrogen, $C_1-C_4$-alkyl, $C_3-C_6$-alkenyl or $C_3-C_6$-alkynyl, and $R^4$ is hydrogen, $C_1-C_4$-alkyl, $C_3-C_6$-alkenyl, $C_3-C_6$-alkynyl, $C_1-C_6$-acyl or benzoyl which in turn, is unsubstituted or substituted by from one to three of the following substituents: nitro, cyano, halogen, $C_1-C_4$-alkyl, $C_1-C_4$-alkoxy, $C_1-C_4$-alkylthio or $C_1-C_4$-hatoalkyl, or their agriculturally useful salts, esters of $C_1-C_{10}$-carboxylic acids or inorganic acids.

2. A herbicidal composition which comprises an effective amount of a compound of the formula I as set forth in claim 1 and inert additives.

3. A method of combating the growth of unwanted plants, wherein the unwanted plants and/or their habitat are treated with a herbicidally effective amount of a cyctohexenone derivative of the formula I as set forth in claim 1.

* * * * *

UNITED STATES PATENT AND TRADEMARK OFFICE
CERTIFICATE OF CORRECTION

PATENT NO.: 5,411,936

DATED: May 2, 1995

INVENTOR(S): KAST et al.

It is certified that error appears in the above-identified patent and that said Letters Patent is hereby corrected as shown below:

On the cover page, item [57], line 10 after the formula, "$C_1$-$C_6$-alkoxy-$C_1$-$C_6$-alkyl" should read --$C_1$-$C_4$-alkoxy-$C_1$-$C_6$-alkyl--.

Column 32, line 55, claim 1, "$C_1$-$C_4$-hatoalkyl" should read --$C_1$-$C_4$-haloalkyl--.

Column 32, line 64, claim 3, "cyctohexenone" should read --cyclohexenone--.

Signed and Sealed this

Twenty-seventh Day of June, 1995

Attest:

BRUCE LEHMAN

*Attesting Officer*  *Commissioner of Patents and Trademarks*